United States Patent [19]

Vitello et al.

[11] Patent Number: 4,667,837
[45] Date of Patent: May 26, 1987

[54] TAMPER PROOF CAP

[75] Inventors: John P. Vitello, Weston; George W. Routhier, Braintree; Daniel P. McCrory, Plainville, all of Mass.

[73] Assignee: International Medical Industries, Incorporated, Watertown, Mass.

[21] Appl. No.: 870,867

[22] Filed: Jun. 5, 1986

[51] Int. Cl.[4] .............................................. B65D 41/32
[52] U.S. Cl. .................................... 215/228; 206/564; 206/445; 215/230; 215/253; 604/111
[58] Field of Search ................ 604/111; 215/228, 230, 215/253; 206/445, 564

[56] References Cited

U.S. PATENT DOCUMENTS

| | | | |
|---|---|---|---|
| 3,245,567 | 4/1966 | Knight | 215/253 |
| 3,747,751 | 7/1973 | Miller et al. | 206/564 X |
| 4,216,872 | 8/1980 | Bean | 215/253 |
| 4,313,539 | 2/1982 | Raines | 206/445 X |
| 4,420,085 | 12/1983 | Wilson et al. | 206/564 X |
| 4,571,242 | 2/1986 | Klein et al. | 604/111 |

Primary Examiner—Donald F. Norton

[57] ABSTRACT

A stop member for a device such as a syringe is inaccessibly disposed in a sleeve member. The ring member is also disposed about a portion of the stop member and in the sleeve member. The ring member is connected to the inside of the sleeve member by means of a frangible connection. When the sleeve member is twisted, the sleeve member and its connected ring member freely rotate about a portion of the stop member at the end of the syringe. When the sleeve member is axially pulled off the end of the syringe, the frangible connection breaks, and the sleeve member is removed, leaving the ring member and stop member disposed on the end of the syringe thereby indicating that the prefilled syringe has been tampered with.

18 Claims, 6 Drawing Figures

TAMPER PROOF CAP

BACKGROUND OF THE INVENTION

The present invention relates to a tamper proof cap which provides a visual indication when the associated prefilled device has been tampered with.

More particularly, the present invention relates to a tamper proof cap for a prefilled syringe.

Syringes prefilled from a central location have become commonplace in a hospital environment in order to control and monitor drugs or other medications which are administered as injectables, i.e. by way of syringes and needles. This method of drug delivery is known as unit dose dispensing. In addition to reducing errors in medication and dosage, better control of inventory and monitoring of usage of drugs, such as controlled substance drugs, is achieved with unit dose dispensing.

Prefilled syringes do not generally include needles since the required needle size is determined by the person who administers the injection. Thus, a readily removable syringe cap was used to close the syringe and protect its sterility while in transit to the patient.

Unit dose dispensing has proven to be an improvement in reducing drug delivery errors. However, since the prefilled syringes were handled by several individuals prior to injection, the uncertainty remained that the drug or medication in the prefilled syringe had been inadvertantly or purposefully tampered with before it was actually administered to the patient. Without an accurate indication as to whether or not the prefilled syringe has been tampered with, it is impossible to determine if the drug had been adulterated or if a prefilled syringe is suitable for rerouting to another patient.

A prior art attempt to provide a tamper proof prefilled syringe utilized a paper, taped over the syringe cap of the prefilled syringe. The paper was torn off to remove the cap and give a visual indication that the prefilled syringe had been opened or otherwise tampered with. Another prior art approach called for packaging the entire prefilled syringe in a bulky plastic bag which was heat sealed. Neither of these solutions proved satisfactory in that they were cumbersome to use and involved additional components, i.e. the tape or bag.

Briefly stated and according to an embodiment of this invention, the problems with the prior art devices have been overcome by the practice of this invention which includes a liquid-impervious closure or stop member providing a removable friction fit with the exit port of a device, such as a syringe, having a liquid reservoir. The stop member is inaccessibly disposed in a cylindrical sleeve member. A cylindrical ring member is concentrically disposed within the sleeve member and about a portion of the stop member. The ring member is connected to the sleeve member by one or more frangible or breakable connections which provide a mechanical coupling with the sleeve member when the sleeve member is twisted, thereby causing the sleeve member to rotate about the end of the syringe or the like.

When the sleeve member is pulled, in an axial direction, off the device, with a force less than the frictional force connecting the stop member with the exit port of the liquid reservoir, the frangible connection is broken and the sleeve member becomes free, thereby indicating that the device which includes the liquid reservoir has been tampered with. The remaining ring member may include an identification portion for inventory control or, for example, to indicate a type, origin, and/or date of the medication.

A support member may form part of a package base for one or more tamper proof caps. The support member provides a friction fit with the sleeve member and traps the stop member between the support member and the ring member. Such a combination provides for the ready coupling of the syringe to the tamper proof cap and the withdrawal of the tamper proof cap from its packaging. In addition, the syringe with its assembled tamper proof cap is designed to be free standing to aid in storage and distribution.

SUMMARY OF THE INVENTION

It is therefore an object of this invention to provide a simple, easy-to-use-and-manufacture, tamper proof cap for a prefilled device.

It is also an object of this invention to provide a tamper proof cap which is leak-free yet capable of providing a clear visual indication if tampered with.

It is another object of this invention to provide a tamper proof cap for a prefilled device which allows the prefilled device to stand up for storage or the like.

It is a further object of this invention to provide a tamper proof cap which is easily coupled to the end of a prefilled device and readily removable from its packaging.

It is a further object of this invention to provide a tamper proof cap for a prefilled device which, once it has been tampered with, leaves a distinct and unmistakable visual indication of that fact.

The invention both as to its organization and principle of operation, together with further objects and advantages thereof, may better be understood by reference to the following detailed description of an embodiment of the invention taken in conjunction with the accompanying drawings in which:

DETAILED DESCRIPTION OF THE PREFERRED EMBODIMENT

Figure 1:
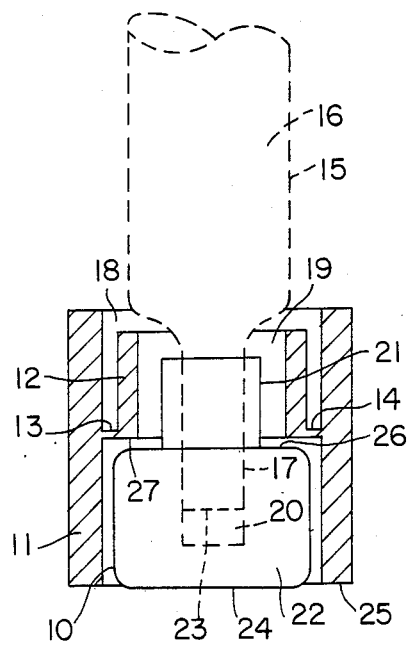
FIG. 1 is a front elevational view, partial in section, of the tamper proof cap, in accordance with this invention.
Figure 2:
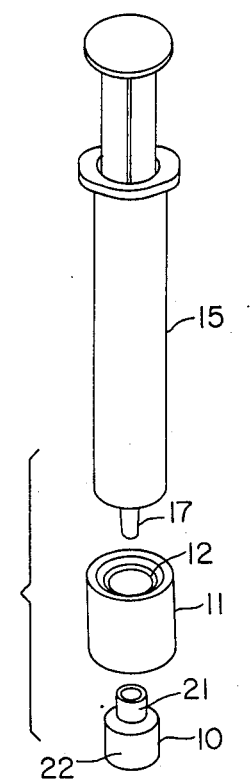
FIG. 2 is an exploded perspective view of the tamper proof cap and a syringe, in accordance with this invention.
Figure 3:
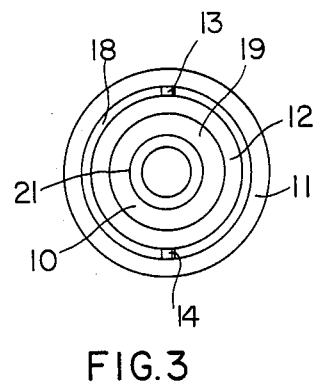
FIG. 3 is a top plan view of the tamper proof cap, in accordance with this invention.

Referring now to the drawings where the same reference number will designate like parts, the tamper proof cap, best seen in FIGS. 1, 2 and 3, is made up of a stop member 10 concentrically disposed, in an inaccessible manner, inside a lower portion of a generally cylindrical sleeve member 11. Concentrically disposed in an upper portion of sleeve member 11 is a generally cylindrical ring member 12. The ring member 12 is preferably totally disposed inside sleeve member 11. Frangible means or breakable connections 13 and 14 each connect a bottom portion of the outer wall of ring member 12 with an approximately mid-location of the inner wall of sleeve member 11, thereby forming, in a preferred embodiment, a one-piece integrally molded unit made up of outer sleeve 11, inner ring 12, and frangible means such as a breakable connections 13 and 14.

Shown in dotted lines, in FIG. 1, is a device, such as a syringe 15, having a liquid reservoir 16 and an exit port or luer tip 17 in fluid communication with the reservoir 16. The syringe 15 is shown as having a standard luer slip tip; however, this invention is also applicable to other syringes, such as luer lock tip syringes.

The luer tip 17, which has an external taper, well known in the art, is inserted through an opened upper end 18, best seen in FIG. 3, of sleeve member 11 and also through an opened upper end 19 of ring member 12 into an internally tapered female opening 20 located in cylindrical flange 21 of stop member 10. The internal tapered opening 20 of stop member 10 may extend into a cylindrical head portion 22 of stop member 10.

The forward end 23 of the luer tip 17 extends into the internal tapered opening 20 of stop member 10 until a frictional fit is achieved. The end 23 of luer tip 17 preferably does not extend to the full depth of the internal tapered opening 20 in order to assure adequate engagement of the luer tip 17 with tapered opening 20 of stop member 10 before the end 23 of luer tip 17 hits the bottom of the tapered opening 20.

The stop member 10 is preferably formed of a one-piece integrally injection-molded plastic such as ABS plastic. Part or all of the head portion 22 of the stop member 10 may be hollow. The head portion 22 of the stop member 10 includes a substantially planar outer surface 24. When the stop member 10 is coupled to the sleeve member 11 and ring member 12 by means of the syringe 15, in a preferred embodiment, the planar outer surface 24 of head portion 22 of stop member 10 is fully disposed within sleeve member 11. Accordingly, the planar outer surface 24 of head portion 22 is approximately coplanar with the plane of an end base rim 25 of sleeve member 11 to permit the assembly to be free standing during storage or the like.

If desired, the stop member 10 may include identification means, such as color coding in order to provide further identification, control or the like. Preferably, the cap 10 is integrally formed with its flange 21 and includes shoulder rim 26 in a plane substantially parallel to planar outer surface 24. The shoulder rim 26 provides an abutting surface with an end base rim 27 of ring member 12 thereby providing a stop. Preferably the outer diameter of the head portion 22 of stop member 10 is greater than the inner diameter of ring member 12 and, of course, less than the inner diameter of sleeve member 11, in order that the stop member 10 be inaccessibly disposed in the sleeve member 11 when coupled to a prefilled device, such as syringe 15.

Sleeve member 11, ring member 12, and breakable connections 13 and 14 are preferably formed as a one-piece integral enclosure manufactured, such as by injection molding. Preferably, the one-piece enclosure is formed of ABS plastic, and the outer wall surface of the ring member 12 includes identification means such as a color coding or the like. Since the inner ring or ring member 12 will be trapped between the stop member 10 and the syringe 15 after the sleeve member 11 is removed, an identification beyond the stop member 10 may be readily realized. Once the stop member 10 is removed, such as by twisting the stop member 10 off of the luer tip 17 of the syringe 15, the ring member 12 may also be removed and discarded, or used as further identification such as inventory control or the like. When the one-piece enclosure is coupled to the syringe 15, it is freely rotatable about a portion of the stop member 10, thereby preventing the accidental twisting off of stop member 10.

Both the one-piece enclosure and the stop member 10 may be formed of a high molecular weight polymer of styrene, polypropylene or a copolymer of styrene.

The frangible means, or breakable connections 13 and 14, are formed of a predetermined strength to assure that the ring member 12 is mechanically coupled to the sleeve member 11 when the sleeve member 11 is twisted or turned about the luer tip 17 of the syringe 15. The frangible means do not provide a mechanical coupling, i.e. they break, when the sleeve member 11 is pulled, in an axial direction such as shown by the arrow A, seen in FIG. 4. The frangible means break when a force is applied which is less than the frictional force which connects the stop member 10 with the exit port, such as luer tip 17, of the prefilled syringe 15.

Figure 4:
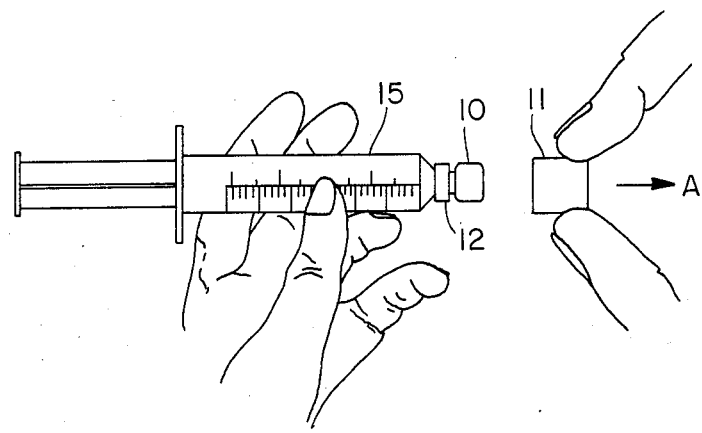
FIG. 4 is a schematic representation showing the removal of the outer sleeve of the tamper proof cap from a prefilled syringe, in accordance with this invention.

Referring to FIG. 4, prefilled syringe 15 is readily held in one hand by the user while the fingers of the other hand grasp the outer wall surface of the sleeve member 11 and axially pull off the sleeve member 11 with sufficient force to cause the frangible means or breakable connections 13 and 14 to break. The breakable connections 13 and 14 are designed to break with a force less than the frictional force which holds the stop member 10 on the exit port of the prefilled syringe 15. Ring member 12 will remain trapped between the stop member 10 and the syringe 15 until removed. Removal of the ring member 12 is accomplished by the user grasping the generally cylindrically shaped head portion 22 of the stop member 10 and gently twisting off the stop member 10 thereby readying the syringe 15 for coupling with a needle of choice.

Once the one-piece enclosure has been attached to the syringe 15, it cannot be readily removed without first breaking a sleeve member 11 away from ring member 12. Thus, tampering is easily detected by visual inspecting. If the outer sleeve member 11 is detached or missing, the syringe 15 has been opened or otherwise tampered with. In addition, if ring member 12 is not trapped between stop member 10 and the syringe 15, the syringe has been tampered with.

Ideally the frangible means includes a first and second breakable member such as breakable members 13 and 14 integrally connected to the ring member 12 and the sleeve member 11 and disposed approximately 180° apart with respect to the ring member 12. Preferably, the ring member 12 is concentrically disposed in the sleeve member 11, and the breakable members 13 and 14 extend at equal lengths between ring members 12 and sleeve member 11. It is within the scope of this invention to have additional frangible members as long as their collective coupling force will be overcome when the sleeve member 11 is pulled, in an axial direction, off the prefilled syringe 15 with a force less than the frictional force connecting the stop member 10 with the exit port of the liquid reservoir 16 of the prefilled syringe 15.

Figure 5:
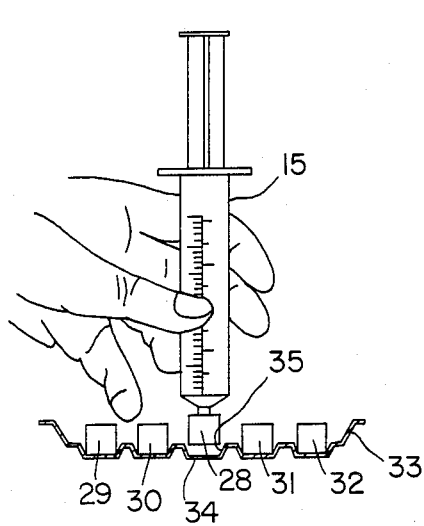
FIG. 5 is a schematic representation showing the assembly of the tamper proof cap on a syringe, in accordance with this invention.
Figure 6:
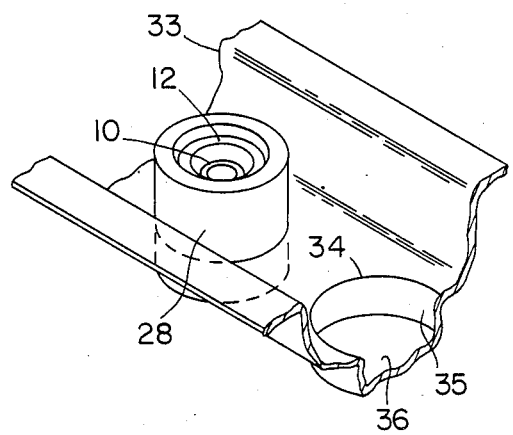
FIG. 6 is a perspective view of two chambers of a support member, in accordance with this invention.

Referring to FIGS. 5 and 6, a plurality of tamper proof caps 28 through 32 are shown frictionally disposed in a packaged sterile blister pack made up of a support member 33 and a removable adhesive cover (not shown). The support member 33 may be formed of clear plastic or the like and include mating circular depressions, such as depression or chamber 34 having a generally upstanding flexible cylindrical wall 35 and a generally planar bottom portion 36. The chamber 34 is dimensioned to frictionally hold a mating tamper proof cap, such as cap 28, since the inner diameter of the cylindrical wall 35 approximate the outer diameter of the sleeve member 11 of the tamper proof cap 28.

The support member 33 is preferably formed of a flexible plastic of sufficient rigidity and shape to permit the holding of the mating tamper proof cap made up of a one-piece integrally molded sleeve/ring combination and a stop member, such as stop member 10, trapped between the bottom portion 36 of chamber 34 and the inner ring member 12. In addition, once the adhesive cover is peeled back to expose one or more tamper proof caps, the exit port, such as luer tip 17 of a mating syringe, such as syringe 15 may readily be aligned and coupled to the chosen tamper proof cap 28 by firmly pushing the syringe tip into the centrally disposed mating flange 21 of stop member 10 and then withdrawing the entire tamper proof cap 28 from the support member 33.

While an embodiment and application of this invention has been shown and described, it will be apparent to those skilled in the art that many more modifications will be possible without departing from the inventive concept herein described. Although the invention is described with respect to a prefilled syringe, other devices for which it is desirable to insure that protective covers have not been removed or tampered with to insure the inner surfaces or contents are sterile and unadulterated, especially medical devices such as stop cocks, intravenous administration equipment, artificial kidney apparatus, etc. are included within the scope of this invention.

What is claimed as new and desired to be secured by Letters Patent of the United States is:

1. A tamper proof cap for a device including a liquid reservoir and an exit port comprising:
   a sleeve member;
   a ring member disposed in said sleeve member;
   a stop member inaccessibly disposed in said sleeve member for providing a removable friction fit, liquid-impervious connection with the exit port of the liquid reservoir; and
   a frangible means connecting said ring member to said sleeve member, said frangible means providing a mechanical coupling with said sleeve member when said sleeve member is twisted, and said frangible means not providing a mechanical coupling with said sleeve member when said sleeve member is pulled, in an axial direction, off the device, with a force less than the frictional force connecting said stop member with the exit port of the liquid reservoir.

2. The tamper proof cap as in claim 1, wherein said sleeve member has an upper and lower portion, said ring member being located in said upper portion of said sleeve member.

3. The tamper proof cap as in claim 2 wherein said stop member includes a generally cylindrical portion disposed in said lower portion of said sleeve member and a concentrically disposed flange portion, said flange portion being disposed in said ring member in said upper portion of said sleeve member.

4. The tamper proof cap as in claim 3, wherein said generally cylindrical portion of said stop member has an outside diameter greater than the inside diameter of said ring member, whereby said stop member is seated on said ring member.

5. The tamper proof cap as in claim 4, wherein said flange portion of said stop member includes an internal tapered female opening for frictionally engaging the exit port of the liquid reservoir.

6. The tamper proof cap as in claim 3 wherein said stop member further includes a generally planar bottom portion integrally connected and transversely disposed to upper cylindrical portion of said stop member, said planar bottom portion of said stop member being substantially within said sleeve member.

7. The tamper proof cap as in claim 2 wherein said frangible means connects the outside of said ring member with the inside of said sleeve member, said frangible means being approximately located between an end of said ring member and the middle of said sleeve member.

8. The tamper proof cap as in claim 7 wherein said frangible means includes a first and second breakable member integrally connected to said ring member and said sleeve member, and disposed approximately 180° apart with respect to said ring member.

9. A tamper proof cap as in claim 1 further including a support member having a generally circular chamber, with a generally cylindrical wall and a generally planar bottom portion, for providing a friction fit to said sleeve member, thereby trapping said stop member between said bottom portion of said chamber and said ring member, and provide ready access for said stop member to frictionally fit with the exit port of the liquid reservoir, whereby when frictional fit is achieved between said stop member and the exit port of the reservoir, said stop member, said ring member, and said sleeve member are readily removable from said support member as a unit.

10. A tamper proof prefilled device comprising:
   a syringe having a liquid reservoir and a luer tip coupled to said reservoir at an end of said syringe;
   a one-piece liquid impervious stop member having a flange portion, said flange portion including an internal tapered female opening frictionally coupled to said luer tip of said syringe;
   a removable sleeve member disposed about said stop member and said luer tip to render said stop member substantially inaccessable when said sleeve member is disposed about said stop member;
   a ring member disposed in said sleeve member and about a portion of said luer of said syringe between said reservoir of said syringe and a portion of said stop member, said ring member also being disposed about said flange portion of said stop member; and
   frangible means connecting said ring member to said sleeve member, said frangible means providing a mechanical coupling with said sleeve member when said sleeve member is twisted, and said frangible means not providing a mechanical coupling with said sleeve member when said sleeve member is pulled, in an axial direction off said luer tip of said syringe, with a force less than the frictional force connecting said stop member with said luer tip of said syringe, said ring member remaining coupled about said luer tip of said syringe when said sleeve member is removed.

11. The tamper proof prefilled device of claim 10 wherein a portion of said sleeve member and a portion of said stop member are substantially coplanar and of a predetermined size to support the standing of the prefilled device.

12. A tamper proof cap for a device comprising:
   a one-piece integrally formed enclosure including an outer sleeve having an inner and outer wall surface, and a concentrically disposed inner ring, having an inner and outer wall surface, and a breakable connection means, said breakable connection means providing a breakable mechanical connection between said outer wall surface of said inner ring and said inner wall surface of said outer sleeve; and
   a one-piece integrally formed stop member having a flange portion for providing a friction fit seal for the device, said flange portion being disposed in said inner ring of said one-piece enclosure, whereby said one-piece enclosure is rotatably disposed about said stop member, said breakable connection means not providing any mechanical coupling with said outer sleeve when said outer sleeve is pulled, in an axial direction, off the device, with a force less than the frictional fit force connecting said stop member to the device, said inner ring remaining coupled to the device when said sleeve is removed.

13. The tamper proof cap as in claim 12 wherein said stop member includes an identification means.

14. The tamper proof cap as in claim 12 wherein said inner ring includes an identification means.

15. The tamper proof cap as in claim 14 wherein said stop member includes an identification means.

16. The tamper proof cap as in claim 12 wherein said one-piece enclosure is formed of a high molecular weight polymer of styrene, polypropylene or a copolymer of styrene.

17. The tamper proof cap as in claim 12 wherein said breakable connection means includes a first and second frangible member disposed approximately 180° apart with respect to said inner ring.

18. The tamper proof cap as in claim 17 wherein said first and said second frangible members extend at equal lengths between said inner ring and said outer sleeve.

* * * * *